United States Patent [19]

Fujiwara et al.

[11] 4,421,911
[45] Dec. 20, 1983

[54] DEOXYDESMYCOSIN

[75] Inventors: Tatsuro Fujiwara, Shizuoka; Eiichi Honda, Mishima; Hideo Sakakibara, Mishima; Takao Hirano, Shizuoka, all of Japan

[73] Assignee: Toyo Jozo Kabushiki Kaisha, Shizuoka, Japan

[21] Appl. No.: 358,805

[22] Filed: Mar. 16, 1982

[30] Foreign Application Priority Data

Mar. 16, 1981 [JP] Japan ............................ 56-38375

[51] Int. Cl.³ .................... C07H 17/08; A61K 31/71
[52] U.S. Cl. ................................. 536/7.1; 424/180
[58] Field of Search .................................... 536/7.1

[56] References Cited

U.S. PATENT DOCUMENTS 4,205,163  5/1980  Mori et al. ........................ 536/7.1
4,255,564  3/1981  Umezawa et al. ................ 536/7.1
4,268,665  5/1981  Sakakibara et al. .............. 536/7.1

FOREIGN PATENT DOCUMENTS 2058765  4/1981  United Kingdom ............. 536/7.1

Primary Examiner—Johnnie R. Brown

Attorney, Agent, or Firm—Young & Thompson

[57] ABSTRACT

A compound of the formula

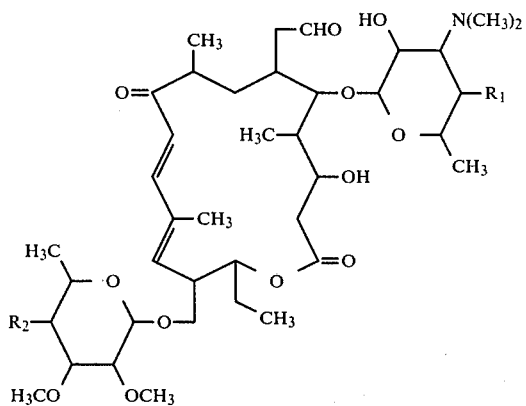

wherein $R_1$ and $R_2$ are hydrogen or hydroxy and at least one of $R_1$ and $R_2$ is hydrogen, or a pharmaceutically acceptable salt thereof, has strong antimicrobial and antibacterial activity..

4 Claims, No Drawings

DEOXYDESMYCOSIN

This invention relates to novel derivatives of the antibiotic tylosin. More particularly, the invention relates to compounds of the formula

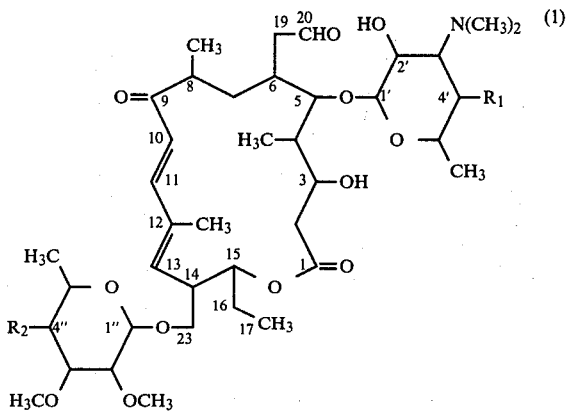

wherein $R_1$ and $R_2$ are hydrogen or hydroxy and at least one of $R_1$ and $R_2$ is hydrogen, and to the pharmaceutically acceptable salts thereof.

Examples of the salts are salts with inorganic acids such as hydrochloric acid, sulfuric acid or phosphoric acid, or salts with organic acids such as acetic acid, propionic acid, tartaric acid, citric acid, succinic acid, malic acid, aspartic acid, or glutamic acid. Other non-toxic salts can also be used.

The above novel compound [1] has strong antimicrobial activity against Gram positive bacteria as compared with the starting material tylosin and desmycosin [4'-demycarosyl tylosin, *Antibiotics and Chemotherapy*, 11 (5), 328–334 (1961)]. Also the antibiotic of the present invention has strong antibacterial activity against clinical isolates of macrolide antibiotics resistant strains group A (clinical isolates of erythromycin, oleandomycin and 16-membered macrolide antibiotics resistant strains), and may have curative effects on clinical infectious diseases. It is also useful as chemotherapeutical agents for animals and for feed additives.

In the present invention, compound [1] and its intermediates are designated according to the numbering of compound [1].

The compounds of the present invention can be prepared by the following methods:

(A) A compound [1] wherein $R_1$ is hydroxy and $R_2$ is hydrogen, i.e. 4"-deoxy-desmycosin.

This compound can be prepared by diacetylating the hydroxy group at positions -2' and -4', trifluoromethanesulfonilating the hydroxy group at position -4" of the thus-obtained 2', 4'-O-diacetyl, halogenating at position -4" the thus-prepared 2', 4"-O-diacetyl-4"-halogenodesmycosin and de-diacetylating the thus-obtained 2', 4'-O-diacetyl-4"-deoxy-desmycosin.

The above diacetylation is performed by reaction with acetic anhydride in an inert organic solvent for desmycosin. Examples of inert organic solvents are dichloromethane, chloroform, dichloroethane or acetone. The reaction proceeds at room temperature, and the reaction process can be checked by silica gel thin layer chromatography (TLC). The reaction can be terminated upon the disappearance of desmycosin. Desmycosin has four hydroxy groups at positions -3, -2', -4' and -4"', and acetyl groups can be selectively introduced at positions -2' and -4' by the above reaction.

The above trifluoromethanesulfonylation can be achieved by reacting 2', 4'-O-diacetyl-desmycosin with trifluoromethanesulfonic anhydride [$(F_3CSO_2)_2O$] in an inert organic solvent in the presence of a tertiary organic amine. Preferred examples of inert organic solvents are dichloromethane, chloroform, dichloroethane or acetone. Examples of tertiary organic amines are pyridine, picoline, collidine, N-methylmorpholine or dimethylaniline, and the most preferred example is pyridine. The reaction proceeds at a temperature below room temperature. The reaction process can be checked by silica gel TLC, and can be terminated upon the disappearance of 2', 4'-O-diacetyl-desmycosin.

The above 4"-halogenation can be achieved by reacting 2',2'-O-diacetyl-4"-O-trifluoromethanesulfonyl-desmycosin with an alkali halide in an inert organic solvent. Examples of inert organic solvents are dimethoxyethane and acetone. Examples of alkali halides are alkali iodide, alkali bromide, alkali chloride and alkali fluoride. Preferred examples are alkali iodides such as NaI, KI or LiI. The reaction proceeds under heating at a temperature below the boiling point of the conventional organic solvents. The reaction process can be checked by silica gel TLC and can be terminated upon the disappearance of 2',4'-O-diacetyl-4"-O-trifluoromethanesulfonyl-desmycosin.

The above dehalogenation at position-4" can be achieved by reacting 2',4'-O-diacetyl-4"-deoxy-4"-halogeno-desmycosin with tributyl tin hydride and a catalytic amount of azo-bisisobutylonitrile in an inert organic solvent. Examples of inert organic solvents are preferably benzene and toluene. The reaction proceeds at a temperature below the boiling point of the organic solvent under an inert gas such as argon. The reaction process can be checked by silica gel TLC and is terminated upon the disappearance of 2',4'-O-diacetyl-4"-deoxy-4"-halogeno-desmycosin.

The above de-diacetylation can be achieved by treating 2', 4'-O-diacetyl-4"-deoxy-desmycosin with methanol under heating. The reaction process can be checked by silica gel TLC and is terminated upon the disappearance of 2', 4'-O-diacetyl-4"-deoxydesmycosin.

(B) A compound [1] wherein $R_1$ is hydrogen and $R_2$ is hydroxy, i.e. 4'-deoxy-desmycosin:

This compound can be prepared by de-mycarosylating with dilute acid, acetylating the hydroxy group at position-4" of the obtained 2'-O-acetyl-desmycosin, trifluoromethanesulfonylating the hydroxy group at position -4' of the 2', 4"-O-diacetyldesmycosin, iodizing the position -4' of 2', 4"-O-diacetyl-4'-O-trifluoromethanesulfonyl-desmycosin, de-acetylating the position -4" of the 2', 4"-O-diacetyl-4'-deoxy-4'-iodo-desmycosin, and deiodizing the de-2'-acetylating the thus-obtained 2'-O-acetyl-4'-deoxy-4'-iodo-desmycosin.

The above de-4"-mycarosylation can be achieved by hydrolyzing with a dilute acid such as 0.3–0.5 N hydrochloric acid. The reaction proceeds at room temperature and can be checked by silica gel TLC, and is terminated upon the disappearance of 2'-acetyltylosin.

The above acetylation of the 4"-hydroxy group can be performed by treating with acetyl halide in an inert organic solvent in the presence of a tertiary organic amine. Examples of tertiary organic amine are pyridine, picoline, collidine, N-methylmorpholine, N-methylpiperidine and dimethylaniline, and pyridine is advantageous because it can be used as the solvent. An example of acetyl halide is acetyl chloride. The reaction proceeds at room temperature and can be checked by silica gel TLC, and is terminated upon the disappearance of 2'-O-acetyl-desmycosin.

Three hydroxy groups exist at positions -3, -4' and -4" of 2'-O-acetyl-desmycosin, and an acetyl group can be selectively introduced into the hydroxy group at position-4" under the acetylation conditions described hereinabove.

The above trifluoromethanesulfonylation can be achieved by reacting 2', 4"-O-diacetyl-desmycosin with trifluoromethanesulfonylhalide in an inert organic solvent in the presence of a tertiary organic amine. Examples of inert organic solvents are dichloromethane, chloroform and dichloroethane. Examples of tertiary amines are pyridine, picoline, collidine, N-methylmorphorine, N-methylpiperidine, dimethylaniline, triethylamine and dimethylaminopyridine. Pyridine can also be used as the reaction solvent. An example of trifluoromethanesulfonyl halide is trifluoromethanesulfonyl chloride ($CF_3SO_2Cl$). The reaction proceeds at a temperature below room temperature, and can be checked by silica gel TLC. The reaction can be terminated upon the disappearance of 2', 4"-O-diacetyl-desmycosin.

The above iodization at position -4' can be achieved by treating 2', 4"-O-diacetyl-4'-O-trifluoromethanesulfonyl-desmycosin with an alklai iodide in an inert organic solvent. Examples of inert organic solvents are hexamethylphosphoramide (HMPA) and dimethylformamide (DMF). Examples of alkali iodides are NaI, KI and LiI. The reaction proceeds under heating, preferably at 50°-100° C. The reaction process can be checked by silica gel TLC and is terminated upon the disappearance of 2', 4"-O-diacetyl-4'-O-trifluoromethanesulfonyl desmycosin.

The above deacetylation at position-4" can be achieved by treating 2', 4"-O-diacetyl-4'-deoxy-4'-iodo-desmycosin with a diluted methanol solution of $NaOCH_3$. The concentration of the methanol solution of $NaOCH_3$ is 0.05–0.3%. The reaction proceeds at room temperature and can be checked by silica gel TLC. The reaction is terminated upon the disappearance of 2', 4"-O-diacetyl-4'-deoxy-4'-iodo-desmycosin. The reaction can be terminated by adding water.

In the removal of the 2'-acetyl group and 4'-iodo group from the thus-obtained 2'-O-acetyl-4'-deoxy-4'-iodo-desmycosin, the iodine group is preferably removed first. Removal of the iodine can be effected in the same way as dehalogenation at position -4" in the above process (A). Removal of the acetyl group at position -2' can be effected by heating in methanol. The reaction progress can be checked by silica gel TLC and is terminated upon the disappearance of the starting materials.

(C) A compound [1] wherein $R_1$ and $R_2$ are hydrogen, i.e. 4', 4"-di-deoxy-desmycosin:

This compound can be prepared by trifluoromethanesulfonylating the hydroxy group at position -4" of 2'-O-acetyl-4'-deoxy-4'-iodo-desmycosin obtained by process (B) hereinabove, iodizing at position -4" of the thus-obtained 2'-O-acetyl-4'-deoxy-4'-iodo-4"-O-trifluoromethanesulfonyl-desmycosin, and deiodizing and deacetylating at position -2' of the thus-obtained 2'-O-acetyl-4',4"-di-deoxy-4',4"-diiodo-desmycosin.

The above trifluoromethanesulfonylation can be effected in the same way as in process (A) above.

The above iodization at position -4" can be effected in the same way as the 4"-halogenation in process (A) above.

In the removal of the 2'-acetyl group and 4', 4"-di-iodo group in 2'-O-acetyl-4', 4"-di-deoxy-4', 4"-di-iodo-desmycosin, the deiodization reaction is preferably performed first.

Re-iodization is effected in the same way as de-4"-halogenation in process (A) above. The removal of the 2'-acetyl group can be achieved by heating in methanol. The reaction progress can be checked by silica gel TLC and is terminated upon the disappearance of the starting materials.

If reaction intermediates are required to be isolated from the reaction medium, the reaction medium is poured into water, adjusted to pH 9 by adding the alkali such as aqueous ammonia, extracted with a water-immiscible organic solvent such as chloroform, and washed and concentrated to purify the intermediate. Further purification can be achieved by column chromatography using silica gel, active alumina or an adsorption resin.

The product obtained by the processes hereinabove can be purified further by column chromatography.

The minimum inhibitory concentration (MIC) of the compounds of the present invention is illustrated in Table 1.

The following examples illustrate the present invention. In the examples, the Rf values are measured, if not specified, by the following TLC:

Carrier: silica gel (E. Merck A.G., DC-Fertigplatten Kiesel gel 60 F 254, Art 5715)

Developer:
  a. chloroform-methanol-aqueous ammonia (150:10:1)
  b. chloroform-methanol-acetic acid-water (80:7:7:1)
  c. benzene-acetone (4:1)
  d. benzene-acetone (8:1)
  e. hexane-benzene-acetone-ethyl acetate-methanol (90:80:25:60:30)

TABLE 1

| | MIC (μg/ml) | | | | | |
|---|---|---|---|---|---|---|
| | Test sample | | | | | |
| | The compound [1] of the present invention | | | Control | | |
| Test organisms | $R_1$ = OH, $R_2$ = H | $R_1$ = H, $R_2$ = OH | $R_1$ = H, $R_2$ = H | Tylosin | Descomycin | Josamycin |
| Staphylococcus aureus ATCC6538p | 0.4 | 0.8 | 0.4 | 0.8 | 0.8 | 0.4 |
| Staphylococcus aureus MS353 | 0.4 | 0.8 | 0.2 | 1.6 | 0.8 | 0.8 |
| Staphylococcus aureus MS353AO* | 6.3 | 50 | 50 | >100 | >100 | >100 |
| Staphylococcus aureus 0116* | 1.6 | 3.1 | 3.1 | >100 | 3.1 | >100 |
| Staphylococcus aureus 0119* | 1.6 | 6.3 | 12.5 | >100 | >100 | >100 |
| Staphylococcus aureus 0127* | 6.3 | 12.5 | 12.5 | >100 | >100 | >100 |
| Streptococcus pyogenes N.Y.5 | ≦0.05 | 0.1 | ≦0.05 | 0.2 | ≦0.05 | ≦0.05 |

TABLE 1-continued

| | MIC (μg/ml) | | | | | |
|---|---|---|---|---|---|---|
| | Test sample | | | | | |
| | The compound [1] of the present invention | | | Control | | |
| Test organisms | $R_1$ = OH, $R_2$ = H | $R_1$ = H, $R_2$ = OH | $R_1$ = H, $R_2$ = H | Tylosin | Descomycin | Josamycin |
| *Streptococcus pyogenes* 1022* | 3.1 | 3.1 | 25 | >100 | >100 | >100 |

*Macrolide registant strain A group (clinical isolates of erythromycin, oleandomycin and 16-membered macrolide antibiotics registant strains)

EXAMPLE 1

4"-deoxy-desmycosin (1) 2', 4'-O-diacetyl-desmycosin:

Acetic anhydride (3.0 ml) was added to desmycosin (5.0 g, 6.48 mM) dissolved in dichloroethane (25 ml), and the mixture was stirred at room temperature for one hour. Dilute aqueous ammonia was added to the reaction mixture to bring it to pH 9, with shaking. After drying the dichloroethane layer by adding anhydrous magnesium sulfate, the organic layer was dried in vacuo to obtain 2', 4'-O-diacetyl-desmycosin (4.6 g).

TLC: Rfc=0.14, Rfd - 0.04, Rfe - 0.48

Mass (CI): 856 (MH+), 838, 666, 664, 407, 391, 276, 258, 216, 175.

NMR (100MHz, CDCl$_3$) δppm: 1.79 (s., 3H), 2.04 (s., 3H), 2.05 (s.,3H), 2.34 (s.,6H), 3.49 (s.,3H), 3.61 (s.,3H), 4.31 (d.,1H), 4.56 (d.,1H), 4.73 (d.d.,1H), 4.88 (d.d.,1H), 5.00 (1H), 5.91 (d.,1H), 6.29 (d.,1H), 7.33 (d.,1H), 9.67 (s.,1H)

(2) 2', 4'-O-diacetyl-4"-O-trifluoromethanesulfonyl-desmycosin:

Pyridine (1.08 ml) and (CH$_3$SO$_2$)$_2$O (1.81 ml) were added at 0° C. to 2', 4'-O-diacetyl-desmycosin (4.6 g) dissolved in dry dichloroethane (25 ml) and the mixture was stirred at 0° C. for one hour. The reaction mixture was poured into ice water (100 ml) and extracted with chloroform. The chloroform layer was washed with water and dilute aqueous ammonia, dried by adding anhydrous magnesium sulfate, and dried in vacuo to obtain a crude powder of 2', 4'-O-diacetyl-4"-O-trifluoromethanesulfonyl-desmycosin (4.6 g).

TLC: Rfc=0.41

| Elementary analysis [C$_{44}$H$_{68}$NO$_{18}$SF$_3$]: | | | |
|---|---|---|---|
| | C % | H % | N % | F % |
| Found: | 53.49 | 6.94 | 1.42 | 5.77 |
| Calculated: | 53.43 | 7.13 | 1.14 | 5.22 |

NMR (100MHz, CDCl$_3$) δppm: 1.79 (s.,3H), 2.06 (s.,6H), 2.38 (s.,6H), 3.51 (s.,3H), 3.60 (s.,3H), 4.32 (d.,1H), 4.41 (1H), 4.63 (d., 1H), 4.75 (d.d.,1H), 4.89 (d.d.,1H), 5.00 (1H), 5.91 (d.,1H), 6.30 (d.,1H), 7.32 (d.,1H), 9.67 (s.,1H)

(3) 2', 4'-O-diacetyl-4"-deoxy-4"-iodo-desmycosin:

NaI (1.67 g) was added to 2', 4'-O-diacetyl-4"-O-trifluoromethanesulfonyl-desmycosin (2.2 g) dissolved in dry dimethoxyethane (11 ml) and the mixture was stirred at 70° C. for six hours. The reaction mixture was poured into water (100 ml) and extracted with chloroform. The chloroform layer was washed with dilute aqueous ammonia and water, dried by adding anhydrous magnesium sulfate and concentrated in vacuo. The residue dissolved in a small amount of benzene, and purified by silica gel column chromatography (75 g) using benzene-acetone (10:1). The fractions showing Rfc=0.43 were collected and dried in vacuo to obtain 2', 4'-O-diacetyl-4"-deoxy-4"-iodo-desmycosin (338 mg).

TLC: Rfc=0.43, Rfd=0.15, Rfe=0.74

Beilstein reaction: positive

Mass (CI): 966 (MH+), 948, 840, 832, 710, 692, 682, 664, 409, 407, 391, 389, 373, 371, 285, 276, 274, 258.

(4) 2', 4'-O-diacetyl-4"-deoxy-desmycosin:

Catalytic amounts of azo-bis-isobutylnitrile and tributyl halide (33 μl) were added to 2', 4'-O-diacetyl-4"-deoxy-4"-iodo-desmycosin (100 mg, 0.104 mM) dissolved in dry benzene (2 ml) and the mixture was stirred at 60° C. for three hours under a stream of argon. Water was added to the reaction mixture and the mixture was extracted with chloroform. The chloroform layer was dried by adding anhydrous magnesium sulfate and concentrated in vacuo. The residue was purified by silica gel (5 g) column chromatography using benzene-acetone (6:1). The fractions showing Rfc=0.22 were collected, and dried in vacuo to obtain 2', 4'-O-diacetyl-4"-deoxy-desmycosin.

TLC: Rfc=0.22, Rfd=0.05, Rfe=0.59

Mass (CI): 840 (MH+), 822, 276, 258, 159, 127.

(5) 4"-deoxy-desmycosin:

Methanol (10 ml) was added to the 2', 4'-O-diacetyl-4"-deoxy-desmycosin obtained hereinabove and the mixture was refluxed for 16 hours. The reaction mixture was dried in vacuo to obtain 4"-deoxy-desmycosin (41 mg).

TLC: Rfa=0.29, Rfb - 0.18

Mass (CI): 756 (MH+), 738, 597, 581, 563, 407, 301, 389, 192, 174, 159, 127.

NMR (100 MHz, CDCl$_3$) δppm: 1.80 (s.,3H), 2.50 (s.,6H), 3.40 (s.,3H), 3.49 (s.,3H), 4.25 (d.,1H), 4.64 (d.,1H), 5.02 (1H), 5.93 (d.,1H), 6.25 (d.,1H), 7.32 (d.,1H), 9.69 (s.,1H).

EXAMPLE 2

4'-deoxy-desmycosin (1) Acetic anhydride (25 ml) was added to tylosin (60 g) dissolved in acetone (300 ml) and the mixture was stirred at room temperature for 1.5 hours. The reaction mixture was poured into ice water (3 lit.), adjusted to pH 9 by adding aqueous ammonia, and the sedimented 2'-O-acetyl-tylosin was collected. The precipitate was dissolved in 0.4 N hydrochloric acid (500 ml) and stirred for one hour. The reaction mixture was adjusted to pH 9 by adding dilute aqueous ammonia and extracted with chloroform (500 ml). The chloroform layer was washed with water, dried by adding anhydrous magnesium sulfate, then dried in vacuo to obtain a crude powder of 2'-acetyl-desmycosin (53 g). This powder was dissolved in dry dichloroethane (250 ml), and pyridine (13 ml) and acetyl chloride (9.3 ml) were added thereto and the mixture was stirred at room temperature for one hour. The reaction mixture was poured into ice water (2.5 lit.), adjusted to pH 9 by adding aqueous ammonia and extracted with chloroform (250 ml). The chloroform layer was washed with water, dried by adding anhydrous magnesium sulfate, and concentrated in vacuo. The residue was purified by silica gel (1.5 kg) column chromatography using benzene-acetone (5:1). The fractions showing Rfe=0.42 were collected and dried in vacuo to obtain a white powder of 2′, 4′-O-diacetyl-desmycosin (15.2 g).

TLC: Rfc=0.07, Rfd=0.01, Rfe=0.42

Mass (MI): 856 (MH+), 838, 622, 390, 235, 218, 217.

NMR (100 MHz, CDCl$_3$) δppm: 1.79 (s.,3H), 2.07 (s.,3H), 2.11 (s.,3H), 2.40 (s.,6H), 3.48 (s.,3H), 3.52 (s.,3H), 4.32 (d.,1H), 4.45 (d.d.,1H), 4.63 (d.,1H), 4.8~5.2 (2H), 5.90 (d.,1H), 6.29 (d.,1H), 7.32 (d.,1H), 9.68 (s.,1H)

(2) 2′, 4″-O-diacetyl-4′-O-trifluoromethanesulfonyl-desmycosin:

Triethylamine (1 ml), dimethylaminopyridine (83 mg) and CF$_3$SO$_2$Cl (0.72 ml) were added to 2′, 4″-O-diacetyl-desmycosin (2.32 g, 2.71 mM) dissolved in dry pyridine (9 ml) and the mixture was stirred at 0° C. for two hours.

The reaction mixture was poured into ice water (300 ml), adjusted to pH 9 by adding aqueous ammonia and the precipitate was collected. The precipitate dissolved in chloroform (100 ml) was washed with 0.1 N-hydrochloric acid, water and dilute aqueous ammonia, dried by adding anhydrous magnesium sulfate, and dried in vacuo to obtain a crude powder of 2′, 4″-O-diacetyl-4′-O-trifluoromethanesulfonyl-desmycosin (2.6 g).

TLC: Rfc=0.53, Rfd=0.17, Rfe - 0.78

| Elementary analysis [C$_{44}$H$_{68}$O$_{18}$NSF$_3$]: | | | | |
|---|---|---|---|---|
| | C % | H % | N % | S % | F % |
| Found: | 53.49 | 6.94 | 1.42 | 5.77 | 3.24 |
| Calculated: | 53.77 | 7.15 | 1.16 | 5.26 | 3.13 |

NMR (100 MHz, CDCl$_3$) δppm: 1.80 (s.,3H), 2.10 (s.,3H), 2.11 (s.,3H), 2.43 (s.,6H), 3.48 (s.,3H), 3.54 (s.,3H), 4.36 (d.,1H), 4.45 (d.d.,1H), 4.63 (d.,1H), 4.8~5.2 (3H), 5.90 (d.,1H), 6.29 (d.,1H), 7.32 (d.,1H), 9.67 (s.,1H)

(3) 2′, 4″-O-diacetyl-4′-deoxy-4′-iodo-desmycosin:

NaI (1.52 g) was added to 2′, 4″-O-diacetyl-4′-O-trifluoromethanesulfonyl-desmycosin (2.0 g) dissolved in hexamethylphosphorotriamide (8 ml), and the mixture was stirred at 70° C. for 40 hours. The reaction mixture was poured into water (200 ml), adjusted to pH 9 by adding dilute aqueous ammonia, and the precipitate was collected. The precipitate, dissolved in chloroform (50 ml), was washed with water, dried by adding anhydrous magnesium sulfate and concentrated in vacuo. The residue was purified by silica gel (70 g) column chromatography using benzene-acetone (9:1). The fractions showing Rfc=0.59 were collected and concentrated in vacuo to obtain 2′, 4″-O-diacetyl-4′-iodo-desmycosin (260 mg).

TLC: Rfc=0.59, Rfd=0.22, Rfe=0.80

Beilstein reaction: positive

Mass (CI): 966 (MH+), 948, 650, 623, 605, 407, 389, 371, 344, 326, 217, 198.

(4) 2′-O-acetyl-4′-deoxy-4′-iodo-desmycosin:

2′, 4″-O-diacetyl-4′-deoxy-4′-iodo-desmycosin (130 mg) was added to 0.14% NaOCH$_3$ methanol solution (1.5 ml) and the mixture was stirred at room temperature for one hour. The reaction was stopped by adding water (20 ml) to the reaction mixture, which was then extracted with chloroform (20 ml). The chloroform layer was washed with water, dried by adding anhydrous magnesium sulfate and dried in vacuo to obtain 2′-O-acetyl-4′-deoxy-4′-iodo-desmycosin (110 mg).

TLC: Rfc=0.27, Rfd=0.07. Rfe=0.61

(5) 4′-deoxy-desmycosin:

Catalytic amounts of azo-bis-isobutylnitrile and tributyl tin hydride (37.8 μl) were added to 2′-O-acetyl-4′-deoxy-4′-iodo-desmycosin dissolved in dry benzene (2.2 ml) and the mixture was stirred at 60° C. for three hours under a stream of argon. Chloroform (20 ml) was added to the reaction mixture, which was then washed with dilute aqueous ammonia, dried by adding anhydrous magnesium sulfate and concentrated in vacuo. The residue was purified by silica gel (5 g) column chromatography using benzeneacetone (2:1). The fractions showing Rfe=0.17 were collected and concentrated in vacuo. Methanol (10 ml) was added to the residue and the mixture was refluxed for 16 hours. The reaction mixture was dried in vacuo to obtain 4′-deoxy-desmycosin (37 mg).

TLC: Rfa=0.38, Rfb=0.15

Mass (CI): 756 (MH+), 738, 582, 564, 547, 407, 391, 389, 175, 174, 158

NMR (100 MHz, CDCl$_3$) δppm: 1.77 (s.,3H), 2.26 (s.,6H), 3.49 (s.,3H), 3.61 (s.,3H), 4.20 (d.,1H), 4.56 (d.,1H), 4.98 (1H), 5.92 (d.,1H), 6.28 (d.,1H), 7.34 (d.,1H), 9.70 (s.,1H)

EXAMPLE 3

4′, 4″-di-deoxy-desmycosin (1) 2′-O-acetyl-4′, 4″-di-deoxy-4′, 4″-di-iodo-desmycosin:

Pyridine (0.59 ml) and CF$_3$SO$_2$Cl (0.99 ml) were added to 2′-O-acetyl-4′-deoxy-4′-iodo-desmycosin (2.72 g) dissolved in dry dichloroethane (14 ml), and the mixture was stirred at 0° C. for one hour. The reaction mixture was poured into ice water (60 ml) and extracted with chloroform. The chloroform layer was washed with water and dilute aqueous ammonia, dried by adding anhydrous magnesium sulfate and dried in vacuo to obtain 2′-O-acetyl-4′-deoxy-4′-iodo-4″-O-trifluoromethanesulfonyl-desmycosin. This powder was dissolved in dry dimethoxyethane (10 ml), and NaI (2.2 g) was added, and the mixture was stirred at 60° C. for four hours. The reaction mixture was poured into water (100 ml), adjusted to pH 9 by adding dilute aqueous ammonia and extracted with chloroform. The chloroform layer was washed with water, dried by adding magnesium sulfate and concentrated in vacuo. The concentrate was purified by silica gel (150 g) column chromatography using benzene-acetone (20:1). The fractions showing Rfc=0.80 were collected and dried in vacuo to obtain 2′-O-acetyl-4′, 4″-di-deoxy-4′, 4″-di-iodo-desmycosin (439 mg).

TLC: Rfc=0.80, Rfd=0.50, Rfe=0.88

(2) 4′, 4″-di-deoxy-desmycosin:

Catalytic amounts of azo-bis-isobutylnitrile and tributyl tin hydride (0.32 ml) were added to 2′-O-acetyl-4′, 4″-di-deoxy-4′, 4″-diiodo-desmycosin obtained as hereinabove dissolved in dry benzene (10 ml), and the mixture was stirred at 60° C. for three hours under a stream of argon. Water (100 ml) was added to the reaction mixture and the mixture was extracted with chloroform (100 ml). The chloroform layer was dried by adding anhydrous magnesium sulfate and concentrated in vacuo. The residue was purified by silica gel (20 g) column chromatography using benzeneacetone (3:1). The fractions showing Rfe=0.24 were collected and dried in vacuo to obtain 2'-O-acetyl-4', 4"-di-deoxy-desmycosin. Methanol (40 ml) was added to this powder and the mixture was refluxed for 16 hours. The reaction mixture was dried in vacuo to obtain 4', 4"-di-deoxy-desmycosin (198 mg).

TLC: Rfa=0.49, Rfb=0.19

Mass (CI): 740 (MH+), 722, 608, 606, 582, 565, 407, 391, 373, 175, 174, 159, 158, 127

NMR (100 MHz, CDCl3): δppm: 1.78 (s.,3H), 2.26 (s.,6H), 3.40 (s.,3H), 3.48 (s.,3H), 4.20 (d.,1H), 4.64 (d.,1H), 5.00 (1H), 5.95 (d.,1H), 6.28 (d.,1H), 7.33 (d.,1H), 9.70 (s.,1H)

What is claimed is:

1. A compound of the formula

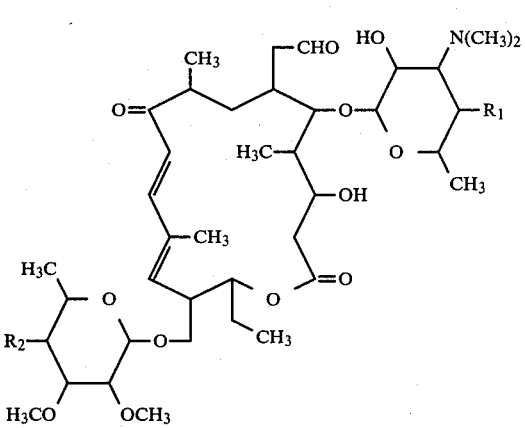

wherein $R_1$ and $R_2$ are hydrogen or hydroxy and at least one of $R_1$ and $R_2$ is hydrogen, or a pharmaceutically acceptable salt thereof.

2. A compound claimed in claim 1, which is 4'-deoxy-desmycosin.

3. A compound claimed in claim 1, which is 4"-deoxy-desmycosin.

4. A compound claimed in claim 1, which is 4', 4"-dideoxy-desmycosin.

* * * * *